United States Patent [19]
Kosaka et al.

[11] Patent Number: 5,159,397
[45] Date of Patent: Oct. 27, 1992

[54] FLOW IMAGING CYTOMETER

[75] Inventors: Tokihiro Kosaka; Shinichi Ogino, both of Hyogo, Japan

[73] Assignee: TOA Medical Electronics Co., Ltd., Kobe, Japan

[21] Appl. No.: 755,304

[22] Filed: Sep. 5, 1991

[30] Foreign Application Priority Data

Feb. 27, 1991 [JP] Japan .................. 3-33137

[51] Int. Cl.$^5$ .............. G01N 33/48; G01N 21/64; G06K 9/20
[52] U.S. Cl. .................. 356/73; 250/461.2; 356/23; 356/39; 356/417; 382/6
[58] Field of Search .......... 356/23, 72, 73, 39, 356/318, 417; 250/461.2; 382/6

[56] References Cited

U.S. PATENT DOCUMENTS

| | | | |
|---|---|---|---|
| 3,992,112 | 11/1976 | Adrion | 356/39 |
| 4,338,024 | 7/1982 | Bolz et al. | 356/23 |
| 4,786,165 | 11/1988 | Yamamoto et al. | 356/23 |
| 5,093,866 | 3/1992 | Douglas-Hamilton et al. | 382/6 |

*Primary Examiner*—Vincent P. McGraw
*Attorney, Agent, or Firm*—Pearne, Gordon, McCoy & Granger

[57] ABSTRACT

An imaging flow cytometer is provided with a continuous-emission light source for continuously monitoring cells passing through the image capturing area of a video camera for cell-image capturing, and with an excitation light source for picking up a fluorescent image of a cell. When a line sensor monitoring cell passage through the cytometer senses such cell passage, the cell is irradiated with strobe light and then, after waiting for the cell to move a fixed distance, with the excitation light. Thus, a particle analyzer is provided in which an image by white light resulting from the strobe light and a fluorescent image resulting from the excitation light can be captured simultaneously by a single video camera in either upper and lower halves or right and left halves of one imaged frame.

5 Claims, 4 Drawing Sheets

CELL MOVING DISTANCE

NATURAL IMAGE
(Image captured by irradiation with strobe light)

FLUORESCENT IMAGE
(Image captured owing to excitation with near ultraviolet light)

FLOW IMAGING CYTOMETER

BACKGROUND OF THE INVENTION

1. Field of the Invention

This invention relates to a flow imaging cytometer. More particularly, the invention relates to a flow-imaging particle analyzing system in which cells fluorescently stained in a manner suitable for the particular cells of interest are introduced to a flow cell to be formed into a planar sheathed flow and irradiated with white light (strobe light) to obtain an image by white light and excited with laser light to obtain a fluorescent image in a highly efficient manner, and in which the two types of images can be captured simultaneously by a single video camera and subject to analysis.

2. Description of the Prior Art

Attempts have been made to irradiate cells, which have been stained and smeared on a glass slide, with light such as visible light or ultraviolet light under a microscope, capture a fluoresecent image of cells of interest, analyze the resulting image and obtain physiological information relating to the cells. However, a method of this kind is not suited to the analytical processing of a large number of cells in a short time, and analysis using fluorescent images has only limited application.

In another example of the conventional flow cytometer, the cell information is obtained using a gross value of the fluorescence emitted from the fluorescently stained cell. In other words, the fluorescence emitted from each portion of the cell is integrated over the entirety of the cell, and the cell information is obtained in the form of such an integrated value. Though such a method lends itself to analysis of a large number of cells in a short period of time, it is not possible to acquire detailed information as to which portions of individual cells have been stained and caused to emit fluorescence. Consequently, this method is limited in terms of analytical performance.

On the other hand, a cell classifying apparatus that has been put into practical use employs a technique in which cells stained in a manner suitable for a particular cell of interest are introduced to a flow cell to be formed into a planar sheathed flow and irradiated with strobe light, a still picture is obtained by a video camera and image process is applied. However, the state of the art is such that the capturing and analysis of fluorescent images of individual cells using this method have still not reached a practical stage because of problems related to fluorescent imaging sensitivity. The present invention makes use of the technology employed in a flow imaging cytometer of the type having a high image capturing efficiency, as previously proposed in the specification of Japanese Patent Application No. 185794/1990.

SUMMARY OF THE INVENTION

Thus, the art still lacks a definitive flow-imaging particle analyzing system for sensing cells that pass through an image capturing area and irradiating the cells with concentrated exciting light, thereby to assure the required fluorescent intensity and obtain a fluorescent image, and for subjecting the fluorescent image, as well as an image by white light of the cells derived from the conventional white-light source, to highly efficient image capturing and analysis using a single video camera.

Accordingly, an object of the present invention is to provide a flow imaging cytometer which expands upon the idea of the previously proposed (the aforementioned Japanese Patent Application No. 185794/1990, hereinafter referred to as "the earlier application") flow imaging cytometer of the type having a high image capturing efficiency, wherein fluorescence emitted by a fluorescently stained cell is obtained as a two-dimensional image at the same time as an image by white light acquired by conventional strobe-light (white-light) irradiation.

According to the present invention, the foregoing object is attained by providing a flow imaging cytometer comprising a flow cell formed to include a flat flow path for causing a specimen solution containing particle components to be sensed to flow as a flat stream, first and third light sources arranged on a first side of the flow cell for irradiating the specimen solution in the flow cell with pulsed light, first image capturing means arranged on an opposite side of the flow cell for picking up still pictures of the particle components in the specimen solution irradiated by the first and third light sources, a second light source arranged on the first side of the flow cell for irradiating the specimen solution in the flow cell with light continuously, second image capturing means arranged on the opposite side of the flow cell for picking up an image of the specimen solution irradiated by the second light source, processing means for executing prescribed analysis based upon image data from the first and second image capturing means, and control means for detecting the particle components based upon the image data from the second image capturing means, and on the basis of such detection, for causing the third light source to emit light first, followed by the first light source upon passage of a prescribed time, within an image capturing period of the first image capturing means, wherein the first light source is a light source for exciting fluorescence, the third light source is a light source for emitting white light, and the image resulting from the first light source and the image resulting from the third light source are each captured in a different area on a light-detecting surface of the first image capturing means.

The flow imaging cytometer of the present invention is further characterized in that the first image capturing means has a two-dimensional iamge capturing area on the flow of the specimen solution, the second image capturing means has a linear image capturing area on the flow of the specimen solution, the image capturing area of the second image capturing means is formed so as to cross the flow of the specimen solution within the image capturing area of the first image capturing means, the image capturing area of the first image capturing means is divided into a zone which includes, and a zone which does not include, the image capturing area of the second image capturing means, and an image in one of these zones resulting from irradiation by the third light source and an image in the other of these zones resulting from irradition by the first light source are captured by the first image capturing means.

The flow imaging cytometer of the present invention is further characterized by having masking means for masking light irradiating the first image capturing means in such a manner that the two images do not overlap each other on the light-detecting surface of the first image capturing means.

The flow imaging cytometer of the present invention is further characterized by having means for forming the irradiating light from the first light source into an elliptical shape, and in that the light-detecting system of a fluorescent image is provided with an image intensifier operated only when the fluorescent image is captured.

Other features amd advantages of the present invention will be apparent from the following description taken in conjunction with the accompanying drawings.

DETAILED DESCRIPTION OF THE PREFERRED EMBODIMENTS

A preferred embodiment of a flow imaging cytometer according to the present invention will now be described with reference to the drawings. The flow imaging cytometer includes, in addition to the light source (a near infrared semiconductor laser) and line sensor for monitoring passage of cells in the earlier application, and excitation light source for obtaining a fluorescent image, an image intensifier for intensifying the fluorescene, and various mirrors, filters and masks employed so that the fluorescent images as well as a conventional image by white light can be acquired by a single video camera.

Figure 1:
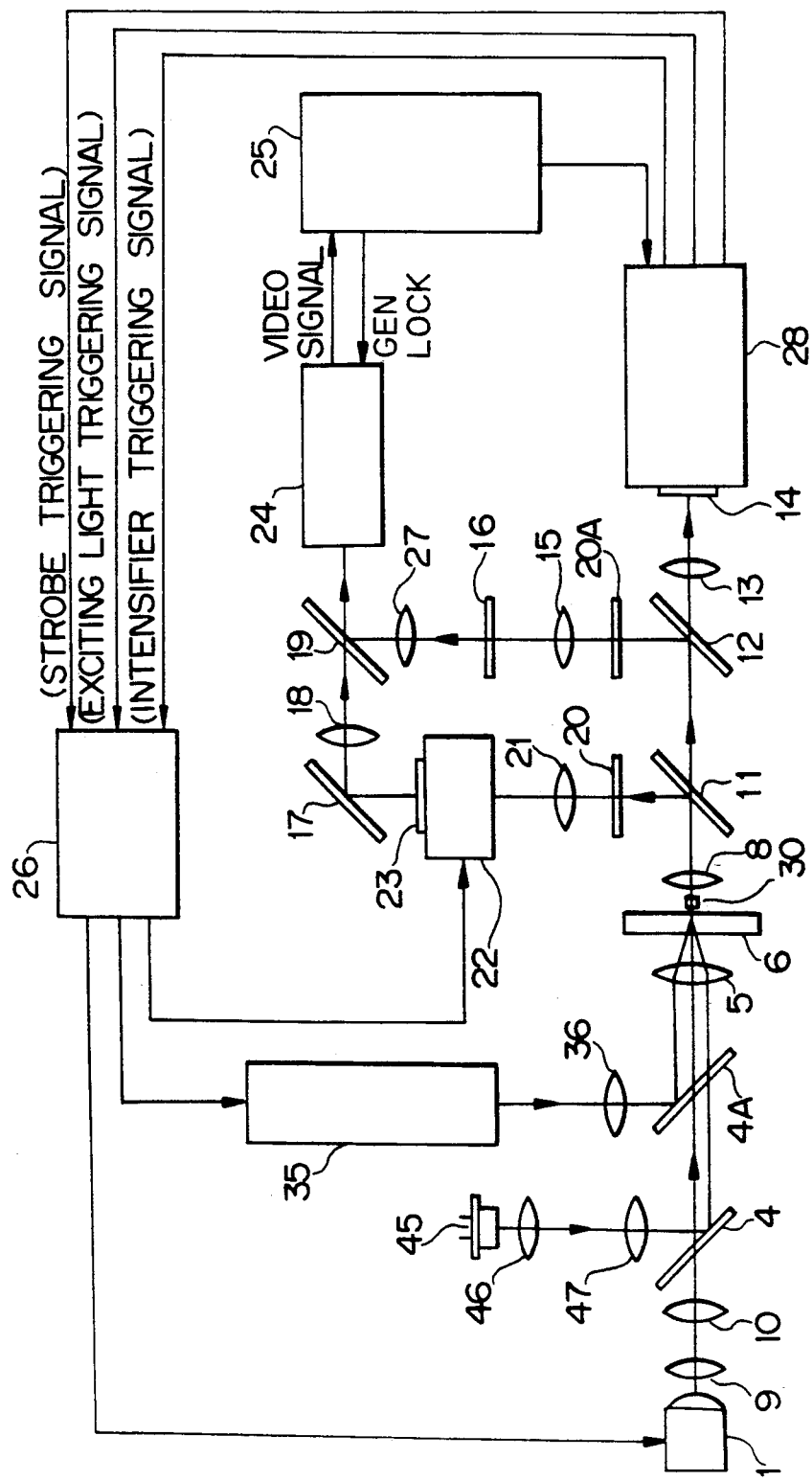
FIG. 1 is a block diagram illustrating the construction of a flow imaging cytometer according to the present invention.
Figure 2:
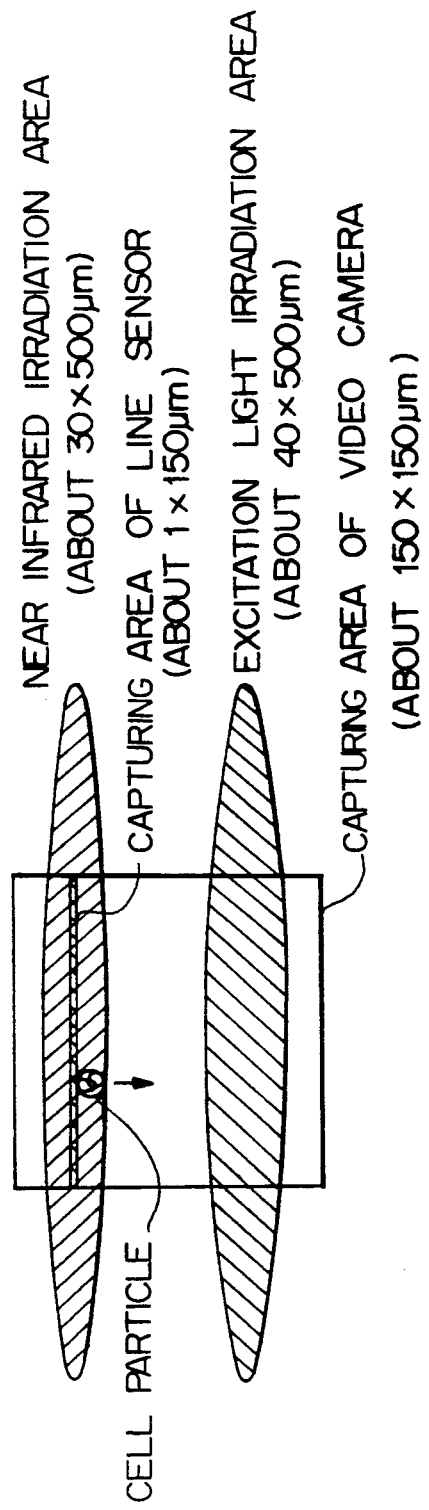
FIG.2 is an explanatory view illustrating an example of a light-irradiating area and an image capturing area of a flow cell.

As shown in FIG. 1, the flow imaging cytometer of the invention includes a planar-sheath flow cell 6 to which a specimen solution containing stained cells is introduced. In order that passage of these cells through an image capturing area of a video camera 24 may be monitored at all times, the image capturing area is irradiated continuously with laser light from a near infrared semiconductor laser 45. The light from the semiconductor laser 45 is collimated by a collimator lens 46, and the collimated light is reflected by a dichroic mirror 4 upon passing through a cylindrical lens 47. The reflected light is stopped down to a finely elongated beam spot perpendicular to the direction of cell move by a condenser lens 5 and irradiates an image capturing area of a line sensor 14, as illustrated in FIG. 2. In this embodiment, the image capturing area of the line sensor 14 is provided slightly above mid-center of the upper half of the image capturing area of video camera 24.

The light from the semiconductor laser 45 leaving the image capturing area passes through an objective lens 8 and is then split by a beam-splitter 11. Part of the light from the beam-splitter 11 passes through a dichroic mirror 12 and enters to a projecting lens 13, which proceeds to form an image on the line sensor 14. The line sensor 14 successively produces voltage outputs conforming to the accumulated amount of photoelectrical conversion of each pixel exposed for a scanning cycle (several tens of microseconds) of one line. By means of signal processing similar to that set forth in the earlier application, a trigger for strobe-light irradiation is applied when a cell crosses the image capturing area of the line sensor 14 during even-numbered field intervals of the video camera 24.

Figure 4:
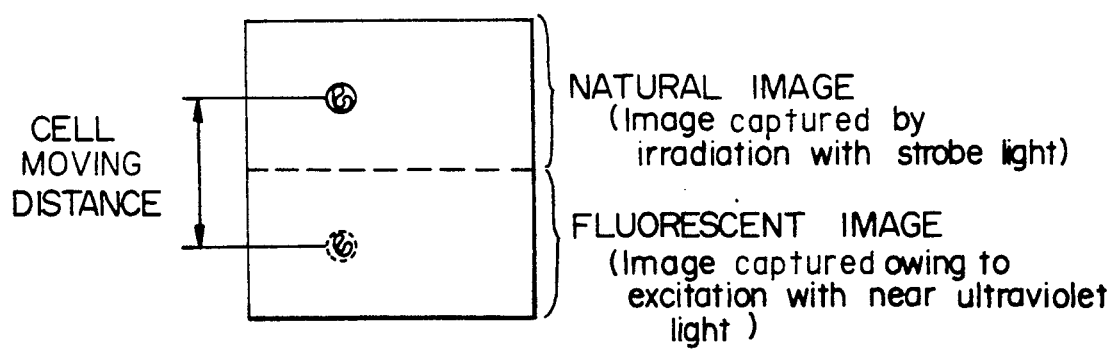
FIG 4 is a diagram showing an example of an imaged frame of a cell captured by a video camera.

The processing time from the instant a cell crosses the image capturing area of the line sensor 14 until a strobe 1 is triggered is 100–200 μsec if the scanning cycle of the line sensor 14 is 50 μsec. On the assumption that the flow velocity of cells in flow cell 6 is 30 mm/sec, a cell will move 3–6 μm in this period of time. Accordingly, the image of a cell obtained by being irradiated with the strobe 1 will always fall in the area located in the upper half of one image frame, as illustrated in FIG. 4.

Figure 5:
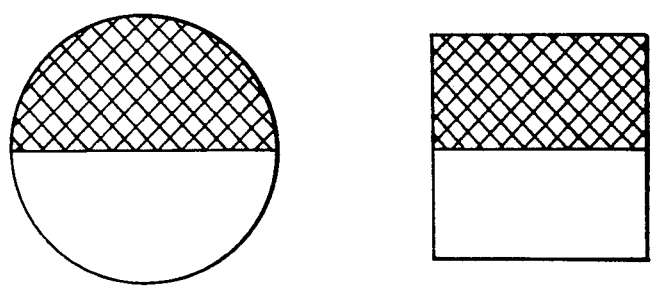
FIG. 5 is a diagram showing examples of semicircular and rectangular masks

The strobe light from strobe 1 is collimated by a collimator lens 9, the collimated light passes through a condenser lens 10 and dichroic mirrors 4, 4A and enters to the condenser lens 5, by virtue of which the entirety of the image capturing area of video camera 24 is irradiated with the strobe light substantially uniformly. This strobe light which has passed through the image capturing area is reflected by the dichroic mirror 12 upon being acted upon by the objective lens 8 and beam-splitter 11. The reflected light has its near infrared component cut by a filter 20A, with the resulting light entering to a projecting lens 15. The latter forms an image upon a semiconductor mask 16, shown in FIG. 5. The lower half of the image is blocked by the mask 16, as a result of which an image is formed on only half of a CCD area sensor of the video camera 24 via a relay lens 27 and half-mirror 19.

The part of the light reflected by the beam-splitter 11 passes through a filter 20 and a projecting lens 21, whereby an image is formed on the photoelectric surface of image intensifier 22. Since gating is applied in such a manner that a voltage is not impressed upon the image intensifier 22 at this point in time, an image does not appear on its output surface. A gating signal for this purpose is produced by a discriminator/controller 28, which is forjudging when a cell has passed through the image capturing area, and for controlling the light sources.

After a cell has been irradiated with light from the strobe 1, the system waits for the cell to travel to a position in the lower half of the image capturing area before irradiating the cell with light from an excitation light source 35 (for example, an He-Cd laser or xenon lamp). A trigger signal for this purpose is produced by the light-source controller 28. The light from the light source 35 is rendered into an oblong form by a cylindrical lens 36, and the light from lens 36 is reflected by the dichroic mirror 4A. The reflected light is stopped down to a finely elongated beam spot perpendicular to the direction of cell move by the condenser lens 5 and irradiates the mid-center region of the lower half of the image capturing area of video camera 24, as depicted in FIG. 2. The cell will be moving through this irradiated area at this time. If the moving speed of the cell through the flow cell 6 is 30 mm/sec and the image capturing area of the video camera 24 has a size of 150×150 μm, then control should be exercised in such a manner that the image capturing area is irradiated with the exciting light approximately 2.5 msec after this area has been irradiated with the light from strobe 1. Since fluorescence is extremely weak, the duration of irradiation with the exciting light should be as long as possible. This will be approximately several tens of microseconds in view of the fact that a longer period of time may result in significant shaking of the image.

To be more precise, the timing for irradiation with the exciting light also must fall within the even-num bered field periods of the video camera 24. Accordingly, the timing at which the strobe light can be emitted when passage of a cell through the image capturing area has been monitored falls within even-numbered fields up to 2.5 msec prior to the odd-number fields.

In operation, fluorescence emitted by a cell in response to irradiation with the exciting light passes through the objective lens 8 and is reflected by the beam-splitter 11, which has a high reflectance. The exciting light which has passed through the image capturing area is intercepted by an exciting light-beam stopper 30, and stray light is removed by the filter 20. Near infrared light continuously emitted in order to monitor cell flow-through also is eliminated by the filter 20.

The fluorescent light which has passed through the filter 20 enters to the projecting lens 21, whereby an image of the cell is formed on the photoelectric surface of the image intensifier 22. At this time a high-voltage is applied to the image intensifier 22 so that the image is intensified by an internal MCP (a microchannel plate) to form an image on the fluorescent output surface of the intensifier. This image, half of which is masked by a semicircular mask 23, is reflected by a mirror 17 so as to pass through a relay lens 18, whereby an image is formed on only half of the CCD area sensor of the video camera 24 through a half-mirror 19.

Meanwhile, the part of the fluorescent light which has passed through the beam-splitter 11 is reflected by the dichroic mirror 12 so that an image is formed at the position of the semicircular mask 16. This image, however, is blocked by the mask. The part of the near infrared light which has passed through the beam splitter 11 is almost totally transmitted by the dichroic mirror 12, and any part thereof reflected by the dichroic mirror 12 is eliminated by the filter 20A. As a consequence, multiple exposure will not take place on the natural-light capturing side of the CCD area sensor of video camera 24 (already irradiated at emission of the strobe light).

Figure 3:
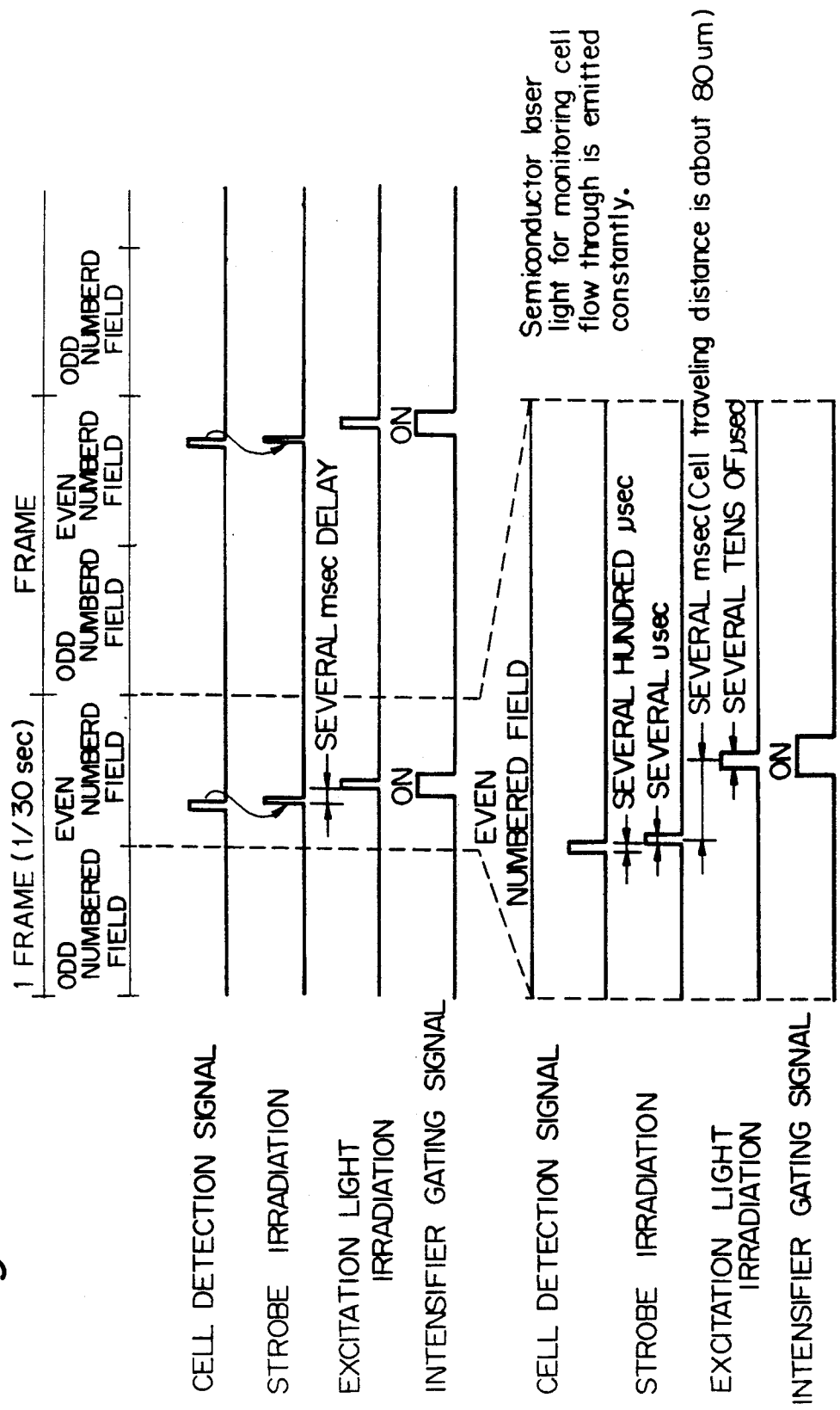
FIG. 3 is a timing chart illustrating irradiation timing and the timing of a gating signal for an image intensifier.

After a cell passing through the image capturing area is detected through a sequence of the above kind, the image by white light and fluorescent image of the cell can be captured by the sole video camera 24. FIG. 4 illustrates an example of such an imaged frame. FIG. 3 is an example illustrating the timing of strobe emission and excitation light emission after detection of a cell passing through the image capturing area, as well as the timing of gating signals for the image intensifier 22. The signals for controlling such timing are produced by the discriminator/controller 28 shown in FIG. 1.

It is required that a cell be irradiated with the excitation light exactly when it has moved to the excitation-light irradiating area after passing through the image capturing area of the line sensor 14. It will suffice if control for such timing entails mere application of a fixed time delay following detection of cell flow-through, provided the flow velocity of the cell does not fluctuate. If flow velocity fluctuates, however, the following expedient can be adopted. Specifically, the position at which the fluorescent image of the cell appears in one frame can readily be determined by image processing. Therefore, if this position shifts from the expected position from one frame to the next, feedback control is applied so as to correct the time delay which elapses until irradiation with the fluorescent light is performed.

In the embodiment described above, the near infrared semiconductor laser 45 is used as the light source for monitoring passage of cells through the image capturing area. However, use can be made of a near infrared LED instead. In addition, the positions at which the fluorescent image light-detecting system and white-light detecting system are disposed in FIG. 1 can be interchanged if desired. Furthermore, an arrangement can be adopted in which, by bringing the fluorescent-light irradiating area to the upper side of the image capturing area in the same manner as the near infrared-light irradiating area, first the fluorescent image is captured after detection of cell flow-through, and then the cell is irradiated with the strobe light after waiting for the cell to move to the lower side of the image capturing area, whereby the image by white light is captured next.

The invention as described above affords the following advantages:

(1) Since passage of cells through the image capturing area is monitored all times, even the images of cells in a weak concentration can be obtained efficiently and with excellent selectivity.

(2) The irradiating light for obtaining the fluorescent image of a cell need not irradiate the entire image capturing area of the video camera; it can be focused to a specific area instead. This makes it possible to raise the intensity of the irradiating light per unit area so that weak fluorescence can be captured as an image even if exposure time is short.

(3) Two images, namely the image by white light and the fluorescent image, can be acquired in one and the same imaged frame by a single video camera. This facilitates image analytical processing and has advantages in terms of cost.

(4) Images of a large number of cells per unit time can be obtained and subjected to analytical processing by flow imaging techniques.

As many apparently widely different embodiments of the present invention can be made without departing from the spirit and scope thereof, it is to be understood that the invention is not limited to the specific embodiments thereof except as defined in the appended claims.

What is claimed is:

1. A flow imaging cytometer comprising:
   a flow cell formed to include a flat flow path for causing a specimen solution containing particle components to be sensed to flow as a flat stream;
   first and third light sources arranged on a first side of said flow cell for irradiating the specimen solution in said flow cell with pulsed light;
   first image capturing means arranged on an opposite side of said flow cell for capturing still pictures of the particle components in the specimen solution irradiated by said first and third light sources;
   a second light source arranged on the first side of said flow cell for irradiating the specimen solution in said flow cell with light continuously;
   second image capturing means arranged on the opposite side of said flow cell for picking up an image of the specimen solution irradiated by said second light source;
   processing means for executing prescribed analysis based upon image data from said first and second image capturing means; and
   light-source control means for detecting the particle components based upon the image data from said second image capturing means, and on the basis of such detection, for causing said third light source to emit light first, followed by said first light source upon passage of a prescribed time, within an image capturing period of said first image capturing means;

wherein said first light source is a light source for exciting fluorescence, said third light source is a light source for emitting white light, and the image resulting from said first light source and the image resulting from said third light source are each captured in a different area on a light-detecting surface of said first image capturing means.

2. The flow imaging cytometer according to claim 1, wherein said first image capturing means has a two-dimensional image capturing area on the flow of the specimen solution, said second image capturing means has a linear image capturing area on the flow of the specimen solution, the image capturing area of said second image capturing means is formed so as to cross the flow of the specimen solution within the image capturing area of said first image capturing means, the image capturing area of said first image capturing means is divided into a zone which includes, and a zone which does not include, the image capturing area of the second image capturing means, and an image in one of these zones resulting from irradiation by said third light source and an image in the other of these zones resulting from irradiation by said first light source are captured by said first image capturing means.

3. The flow imaging cytometer according to claim 2, further comprising masking means for masking light irradiating said first image capturing means in such a manner that the two images do not overlap each other on the light-detecting surface of said first image capturing means.

4. The flow imaging cytometer according to claim 2, further comprising means for forming the irradiating light from said first light source into an elongated elliptical shape.

5. The flow imaging cytometer according to any one of claims 1 through 4, wherein a light-detecting system of a fluorescent image is provided with an image intensifier, and said image intensifier is operated only when the fluorescent image is captured.

* * * * *

UNITED STATES PATENT AND TRADEMARK OFFICE
CERTIFICATE OF CORRECTION

PATENT NO. : 5,159,397

DATED : October 27, 1992

INVENTOR(S) : Tokihiro Kosaka et al

It is certified that error appears in the above-identified patent and that said Letters Patent is hereby corrected as shown below:

Column 1, line 21, delete "fluoresecent" and insert --fluorescent--.

Column 1, line 48, delete "process" and insert --processing--.

Column 2, line 48, delete "image" and insert --image--.

Column 3, line 6, delete "amd" and insert --and--.

Column 3, lines 33-34, delete "fluorescene" and insert --fluorescence--.

Column 4, line 11, delete "image" and isnert --imaged--.

Column 4, line 24, delete "semiconductor" and insert semicircular--.

Column 4, line 37, delete "forjudging" and insert --for judging--.

Signed and Sealed this

Ninth Day of November, 1993

*Attest:*

BRUCE LEHMAN

*Attesting Officer*  Commissioner of Patents and Trademarks